United States Patent [19]
Williams et al.

[11] Patent Number: 6,008,381
[45] Date of Patent: Dec. 28, 1999

[54] PROCESS FOR PREPARING 3-ISOCHROMANONE

[75] Inventors: Alfred Glyn Williams, Bracknell, United Kingdom; Michael Charles Henry Standen, Bucks, Ala.; Nicholas Russell Foster, Bracknell; Raymond Vincent Heavon Jones, Stirlingshire, both of United Kingdom

[73] Assignee: Zeneca Limited, United Kingdom

[21] Appl. No.: 09/202,401

[22] PCT Filed: May 21, 1997

[86] PCT No.: PCT/GB97/01391

§ 371 Date: Dec. 14, 1998

§ 102(e) Date: Dec. 14, 1998

[87] PCT Pub. No.: WO97/48692

PCT Pub. Date: Dec. 24, 1997

[30] Foreign Application Priority Data

Jun. 17, 1996 [GB] United Kingdom .................... 9612623

[51] Int. Cl.[6] .................................................. C07D 311/04
[52] U.S. Cl. .............................................................. 549/290
[58] Field of Search ............................................... 549/290

[56] References Cited

FOREIGN PATENT DOCUMENTS

| | | |
|---|---|---|
| 760968 | 12/1970 | Belgium . |
| 802822 | 12/1968 | Canada . |
| 804045 | 1/1969 | Canada . |
| 4415681 | 11/1995 | Germany . |
| 6804375 | 10/1968 | Niger . |

OTHER PUBLICATIONS

Spangler, R.J. et al, The Pyrolysis of Isochroman–3–one. A Convenient Synthesis of Benzocyclobutene, Communications, pp 107–108 (Feb. 1973).

J. H. Markgraf et al., 3–Isochromanone, Synthetic Communications, pp 139–41 (1972).

Koch, Stacie S. Canan et al, Modified Conditions for Efficient Baeyer–Villager Oxidation With m–CPBA, Synthetic Communications, pp 829–31 (1989).

G. Kraiss et al, Selective Reduction of Diethyl Homophthalate With Diisobutylaluminium Hydride, Tetrahedron Letters, No. 26, pp 2359–60 (May 1973).

V.B Milevskaya et al, Journal of Organic Chemistry, vol. 9, No. 10, Reaction of Homophthalic Acid with Phosphorus Pentachloride, pp 2160–62 (Oct., 1973).

Kikuo Ishizumi et al, Chemistry of Sodium Borohydride and Diborane, IV[1)] Reduction of Carboxylic Acids to Alcohols with Sodium Borohydride through Mixed Carbonic–Carboxylic Acid Anhydrides[2)], Chem. Pharm. Bull., vol. 16, pp. 492–97 (1968).

Chemical Abstracts, vol. 80, No. 7, 36954e (1974).
Chemical Abstracts, RN 95335–46–9 (1997).

*Primary Examiner*—Amelia Owens
*Attorney, Agent, or Firm*—David P. LeCroy

[57] ABSTRACT

3-Isochromanone is prepared by reacting o-tolyacetic acid with sulphuryl chloride in the presence of a free radical initiator, e.g. AIBN, followed by ring closure of the 2-chloromethylphenylacetic acid so formed with a base, e.g. potassium bicarbonate.

9 Claims, No Drawings

PROCESS FOR PREPARING 3-ISOCHROMANONE

This application is a 371 of PCT/GB97/01391 filed May 21, 1997.

This invention relates to a chemical process and more particularly to a process for preparing 3-isochromanone which is useful in the manufacture of certain agricultural products. 3-Isochromanone is a well known compound and a number of methods for its preparation are described in the chemical literature. For example, it can be prepared by (i) the Baeyer-Villiger oxidation of 2-indanone using hydrogen peroxide in sulphuric acid and acetic anhydride (Syn.Commun. 2 [1972], 139; Synthesis [1973], 107) or using 3-chloroperoxybenzoic acid combined with trifluoroacetic acid (Syn.Commun. 9 [1989], 829); (ii) from 2-methoxycarbonylmethylbenzoic acid by (a) treatment with ethylchloroformate in triethylamine and (b) sodium borohydride (Chem. Pharm. Bull.) 16 [1968], 492, 496); or (iii) from isochroman-3-ol and chromium trioxide (Tet.lett. [1973], 2359). It is also known to prepare 3-isochromanone by the bromination of o-tolylacetic acid with N-bromosuccinimide followed by ring closure by boiling the 2-bromomethylphenylacetic acid so formed with potassium hydroxide in ethanol (Zh.Org.Khim. [1973] 9 (10), 2145–9). A disadvantage of this process is the expensive source of halogen, which makes it unattractive on an industrial scale.

According to one aspect of the present invention there is provided a process for the preparation of 3-isochromanone which comprises the steps:
(a) reacting o-tolylacetic acid with sulphuryl chloride in the presence of a free radical initiator; and
(b) treating the 2-chloromethylphenylacetic acid so formed with a base.

The process is represented by the following reaction scheme:

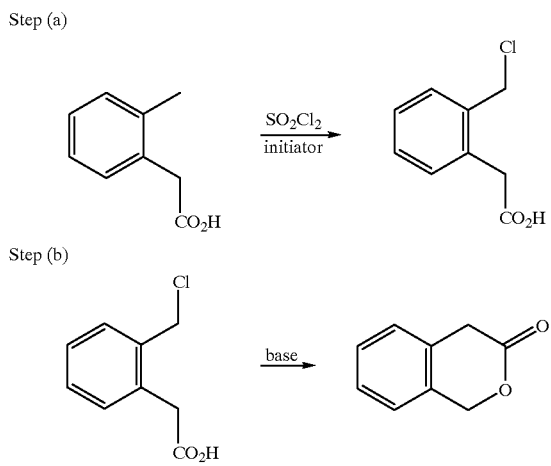

Step (a) of the process is conveniently carried out in a solvent which is inert to the reactants, for example, an aromatic hydrocarbon such as benzene or a halogenated aromatic hydrocarbon such as fluorobenzene or chlorobenzene, at an elevated temperature, suitably from 50° C. to 90° C., for example, from 60° C. to 80° C.

Any amount of sulphuryl chloride may be used but, for efficiency, it is desirable to use at least one mole of sulphuryl chloride per mole of o-tolylacetic acid and preferably a molar excess up to 1.5 moles per mole, for example, up to 1.2 moles per mole. Typically, around 1.1 mole of sulphuryl chloride per mole of o-tolylacetic acid is used.

The free radical initiator may be a suitable source of heat or light or a chemical compound of a type used to initiate free radical reactions, such as a peroxide, a peracid or an azo compound. Particularly suitable is 2,2'-azobisisobutyronitrile (AIBN). The quantity of AIBN used is typically from 0.01 to 0.1 moles per mole of o-tolylacetic acid, for example from 0.01 to 0.05 moles per mole.

Any suitable base may be used in step (b) of the process for example an alkali metal or alkaline earth metal hydroxide, such as sodium or potassium hydroxide. However, it is an advantage of the present process that a mild base such as an alkali metal bicarbonate, for example, potassium bicarbonate, can be used. In this case it may be helpful to use a catalyst to assist ring closure of the 2-chloromethylphenylacetic acid. Thus, a catalytic amount of an iodide, such as an alkali metal iodide, typically potassium iodide, has been found particularly useful. To avoid problems with product crystallisation, it is sensible to treat the product of step (a) with the base at a temperature of from 40° C. to 80° C., suitable from 50° C. to 70° C., a typically at about 60° C.

Both steps of the process are novel and individually form part of the present invention.

Thus, according to another aspect of the present invention there is provided a process for the preparation of 2-chloromethylphenylacetic acid which comprises reacting o-tolylacetic acid with sulphuryl chloride in the presence of a free radical initiator.

Suitably the reaction is carried out in a halogenated aromatic hydrocarbon solvent, for example, fluorobenzene solvent, at a temperature of from 50° C. to 90° C., for example from 60° C. to 80° C.

The amount of sulphuryl chloride used is suitably in the range of from 1 to 1.2 moles per mole of o-tolylacetic acid. The free radical initiator is preferably 2,2'-azobisisobutyronitrile.

The o-tolylacetic acid starting material is a known compound which is commercially available.

In yet another aspect of the present invention there is provided a process for the preparation of 3-isochromanone which comprises treating 2-chloromethylphenylacetic acid with a base.

Suitably the base is an alkali metal or alkaline earth metal hydroxide but is preferably an alkali metal bicarbonate, especially potassium bicarbonate. In a preferred embodiment, the process is carried out at a temperature of from 40° C. to 80° C., more preferably from 50° C. to 70° C. typically at about 60° C. with a catalytic amount of an alkali metal iodide, typically potassium iodide.

In this particular aspect of the invention, the 2-chloromethylphenyl acetic acid may be prepared by the process described in step (a) or by any other method. If it is prepared as described in step (a), it may be isolated first and recrystallised if desired, or used directly in a 'one-pot' process.

In a typical one-pot process, a slurry of o-tolylacetic acid in fluoro- or chlorobenzene is distilled to remove any water and the temperature reduced to the 60–80° C. A chemical initiator (eg AIBN) is added followed by sulphuryl chloride over 3 to 4 hours. the progress of the reaction is monitored by analysing samples of the reaction mixture at suitable intervals using gas chromatography. At the end of reaction an aqueous solution of the base, preferably potassium bicarbonate, is added slowly, optionally with the addition of an iodide catalyst and solid base. The reaction mixture is stirred at around 60° C. for about an hour while samples are taken for analysis. On completion of reaction, the organic and aqueous layers are separated, the organic layer dried by azeotropic distillation and the product precipitated on cooling.

The process of the invention enables 3-isochromanone to be prepared on an industrial scale using a cheap and convenient source of halogen (sulphuryl chloride) for the preparation of the 2-halomethylphenylacetic acid intermediate and a mild base (potassium bicarbonate) for cyclisation. 3-Isochromanone is useful, inter alia, as an intermediate in the manufacture of agricultural products, especially fungicides of the strobilurin type, for example, those described in EP-A-278595.

The invention is illustrated by the following Examples in which:

| | |
|---|---|
| NMR = | nuclear magnetic resonance |
| HPLC = | high performance liquid chromatography |
| s = | singlet | m = | multiplet |
| g = | grammes | kg = | kilogrammes |
| GC = | gas chromatography | | |
| ml = | milliliters | l = | liters |
| mol = | moles | ° C. = | degrees centigrade |
| AIBN = | 2,2'-azobisisobutyronitrile | mp = | melting point |

EXAMPLE 1 o-Tolylacetic acid (750 g at 98%, 4.89 mol) and fluorobenzene (1323 ml) were charged to a 5 liter jacketed vessel equipped with a mechanical agitator, oil circulator, reflux condenser, nitrogen purge and outlets connected to a caustic scrubber to remove hydrogen chloride vapour. The slurry was heated to boiling point and fluorobenzene distilled at atmospheric pressure (200 ml) to remove water. Further fluorobenzene (100 ml) was added to the vessel and distilled to complete the water removal. The dried solution was cooled and stirred overnight under nitrogen.

The fluorobenzene and crystalline solids were re-heated to 80° C. and AIBN (11.3 g) added. Sulphuryl chloride (680.3 g at 97% strength, 4.89 mol) was added over 4 hours using a peristaltic pump and the reaction solution stirred for an hour at 80° C. It was then cooled and left to stand at ambient temperature under nitrogen for two days. A small sample was removed from the mixture, diluted with more solvent and analysed by GC. This showed the presence of 40% starting material. The reaction solution, containing crystalline material, was re-heated to 80° C. Additional sulphuryl chloride was charged (68 g at 97% strength, 0.489 mol) and stirring continued for 1 hour at 80° C. Analysis by GC showed the presence of 23.5% starting material.

The reaction solution was cooled to about 45° C. and saturated potassium bicarbonate solution (908 g) added slowly to avoid the too-rapid evolution of carbon dioxide. Potassium iodide (3.3 g) was added followed by the portionwise addition of solid potassium bicarbonate (430.5 g, 4.3 mol) to give a final pH of 7–8. Water (750 g) was added and the reaction mixture stirred for 15 minutes to dissolve inorganic material and then allowed to settle. The aqueous and organic layers were separated, any residual organic material extracted from the aqueous layer with fluorobenzene (2×500 g) at 60° C. and the organic materials then combined and allowed to cool overnight.

Fluorobenzene (1058 g) was removed from the organic material by atmospheric distillation and methyl cyclohexane (1075 g) charged while maintaining the organic solution at around 80° C. The solution was then allowed to cool and the temperature reduced to around 2° C. once crystallisation had begun. The crystallised 3-isochromanone was isolated by filtration, washed with methylcyclohexane (300 g) and sucked dry: 453.7 g at 96.3% strength (436.91 g 100%); yield 60.4%; m.p. 82.4–83.8° C.

EXAMPLE 2 o-Tolylacetic acid (50 g at 98% strength, 0.326 mol) in fluorobenzene (76.7 g) was dried by azeotropic distillation and cooled to 60° C. AIBN (2.13 g, 0.013 mol) was added in one portion followed by sulphuryl chloride (49.8 g at 97% strength, 0.358 mol) over 3 hours while maintaining the temperature at 60–62° C. A small sample was removed from the mixture, diluted with more solvent and analysed by GC. This showed the presence of 10% o-tolylacetic acid starting material.

A 20% aqueous solution of potassium bicarbonate (60.6 g, 0.121 mol) was added slowly to the reaction mixture followed by potassium iodide (0.22 g) and then, slowly, by solid potassium bicarbonate (20.95 g, 0.209 mol). Stirring was continued for 1 hour at 60° C. Further solid potassium bicarbonate (7.9 g) was added at 60° C. and stirring continued for another 15 minutes. The reaction mixture was left to stand and cool to ambient temperature overnight under nitrogen. It was then warmed to 65° C. and the aqueous and organic layers separated. The organic layer was diluted with fluorobenzene (50 ml), which had been used to wash the separator, and dried by azeotropic distillation. After cyclohexane was added slowly at 60–65° C., the product precipitated on cooling. The temperature was reduced to around 5° C. and the solids filtered and sucked dry to give 27.18 g (100% wt) 3-isochromanone; 56.3% yield; mp 79–80° C.

EXAMPLE 3 o-Tolylacetic acid (150 g at 98% strength, 0.979 mol) and fluorobenzene (280 ml) were charged to a 1 liter 3-necked flask. The contents were heated to remove water by azeotropic distillation and 50 ml of distillates were collected. After cooling under a blanket of nitrogen, the contents of the flask were heated to 78° C. and AIBN (2.25 g) was added. Sulphuryl chloride (204.3 g at 97% strength, 1.468 mol) was added slowly over 3.5 hours under a blanket of nitrogen, keeping the temperature at 78–80° C. Stirring was continued for 1 hour at 80° C. after addition of the sulphuryl chloride. Off gases ($SO_2$ and HCl) were scrubbed with water and caustic soda solution (120 g). A small sample was removed from the mixture, diluted with more solvent and analysed by GC. This showed the presence of 44.35% isochromanone and 54.78% of mono- and dichlorinated starting material. After stirring the reaction mixture for a further hour at 80° C., it was allowed to cool overnight under a blanket of nitrogen. It was then reheated to 60° C. to re-dissolve crystalline material and cooled to 45° C. Potassium iodide (0.66 g) was added followed by the slow additions of saturated sodium bicarbonate solution (165 ml) and solid sodium bicarbonate (143.4 g). Afterwards, the mixture was heated to 60° C. and left stirring for 3 hours.

The organic and aqueous layers were separated at 60° C. Residual organic material was extracted from the aqueous layer with fluorobenzene (2×100 ml) and combined with the main organic layer. Fluorobenzene (238 g) was removed from the organic material by distillation (50° C., >200 mmHg) and methyl cyclohexane (238 ml) added at 60° C. After heating to 80° C., the clear organic solution was cooled to ambient temperature, product beginning to crystallise out at around 50° C. The final orange slurry was cooled to −10° C. using an ice/salt bath and held at −10° C. to −5° C. for 2 hours. The product was then filtered and sucked dry: 87.1 g at 81.2% strength (70.73 g 100%); yield 48.8%.

EXAMPLE 4

This Example illustrates the preparation of 3-isochromanone from recrystallised 2-chloromethylphenylacetic acid using different work-up procedures.

o-Tolylacetic acid (100 g) was slurried in fluorobenzene (153.4 g) under a nitrogen blanket, and heated to reflux. An additional amount of fluorobenzene (100 ml) was then added to the reaction mixture and the solution dried by azeotropic distillation under atmospheric pressure at 85–90° C. The reaction mixture was then cooled to 80° C. and AIBN (2.14 g) was charged to the vessel in one portion. Sulphuryl chloride (105.55 g) was then added to the refluxing reaction mixture (temperature maintained at 80–85° C.) over a period of 3 hours, closely monitoring the progress of the reaction by means of $^1$H NMR. Analysis showed ~80% conversion to 2-chloromethylphenylacetic acid at this point. After the addition was complete, the reaction mixture was allowed to cool slowly to ambient temperature, cooling finally to 0–5° C. The precipitate was filtered by suction, washed with n-hexane (70 g) and pulled dry on the filter, to give a fine off-white powder (75.73 g); $^1$H NMR (CDCl$_3$)δ 3.8(s,2H); 4.6(s,2H); 7.2–7.5(m,4H) ppm; mp 114.5–117.1° C.; quantitative yield 62.15%; % strength 95.7% by $^1$H NMR.

A sample of the 2-chloromethylphenylacetic acid was recrystallised from toluene which, following a hot filtration, gave a white solid of strength 97.75%. Reverse Drown-out Work-up 2-Chloromethylphenylacetic acid (97.75% strength; 10 g) was dissolved in fluorobenzene (20.6 g) at 70° C. over ~20 minutes. The pH of the reaction mixture was found to be 7–8 during the course of the addition. The mixture was then separated at 60° C., the lower aqueous layer being back-extracted with fluorobenzene (10 ml). The combined fluorobenzene phases were then dried by azeotropic distillation at 85–90° C. Slow addition of cyclohexane (20 g) at 80° C. gave a colourless solution which was then slowly cooled to ambient temperature. Further cooling to 0–5° C. gave a white precipitate which was filtered, washed with n-hexane (11.5 g), pulled dry on the filter and dried in air to constant weight (6.60 g); $^1$H NMR (CDCl$_3$)δ 3.7 (s,2H); 5.3(s,2H); 7.2–7.6 (m,4H) ppm; quantitative yield 83.9%; chemical yield 94.8%; % strength 99.7% by quantitative HPLC. Acid Drown-out Work-up 2-Chloromethylphenylacetic acid (97.75% strength; 10 g) was dissolved in fluorobenzene (12.6 g) at 70° C., and aqueous hydrochloric acid (18% strength; 6.45 g) added in one portion. The reaction mixture was stirred at 70–80° C. for 30 minutes. Potassium bicarbonate solution (20% strength; 10.15 g) was then added slowly followed by portionwise addition of solid potassium bicarbonate (6.7 g). The mixture was then separated at 60° C., the lower aqueous layer being back-extracted with fluorobenzene (10 ml). The combined fluorobenzene phases were then dried by azeotropic distillation at 85–90° C. Slow addition of cyclohexane (20 g) at 80° C. gave a colourless solution which was then slowly cooled to ambient temperature. Further cooling to 0–5° C. gave a white precipitate which was filtered, washed with n-hexane (11.5 g), pulled dry on the filter and dried in air to constant weight (6.45 g); $^1$H NMR (CDCl$_3$)δ3.7 (s,2H); 5.3 (s,2H); 7.2–7.6 (m,4H)ppm; quantitative yield 81.9%; chemical yield 99.1%; % strength 99.61% by quantitative HPLC.

EXAMPLE 5

This Example illustrates the preparation of 3-isochromanone from 2-chloromethylphenylacetic acid in the form of an 'end of chlorination' mixture by different work-up procedures.

o-Tolylacetic acid (101 kg; 97.5% strength) was slurried in fluorobenzene (137 kg) in a 4541 glass-lined vessel and the solution heated to 80° C. A moisture content analysis was carried out on the solution and found to be <0.2%. Azeotropic drying was therefore unnecessary. AIBN (2 kg) dissolved in fluorobenzene (25 kg) was then charged via a metering pump over 30 minutes. Following this, sulphuryl chloride (64.51; 108 kg; 98.5% strength) was added to the reaction mixture (temperature maintained at 75–80° C.) over a period of 4 hours. The addition was stopped twice to allow the batch to reheat from 68° C. to 75° C. At the end of the addition, the reaction mixture was sampled to give the 'end of chlorination' mixture. Reverse Drown-out Work-up A sample of the 'end of chlorination' mixture (100 ml; 0.2586 mol) was heated to 65–70° C. and aliquots of this solution were added to a stirred solution of potassium bicarbonate (20% strength; 207.09 g) at 60° C., over 1.5 hours. The mixture was then separated at 60° C., the lower aqueous layer being back-extracted with fluorobenzene (40 ml). The combined fluorobenzene phases were then dried by azeotropic distillation at 85–90° C. Slow addition of cyclohexane (61.4 g) at 80° C. gave a dark red solution which was slowly cooled to ambient temperature. This was after adjusting the fluorobenzene level (25 g), as some fluorobenzene was lost to the atmosphere during the long addition. Further cooling to 0–5° C. gave a beige precipitate which was filtered, washed with n-hexane (26 g), pulled dry on the filter and dried in air to constant weight (19.99 g); $^1$H NMR (CDCl$_3$)δ 3.7 (s,2H); 5.3 (s,2H); 7.2–7.6 (m,4H) ppm; quantitative yield 51.45%; chemical yield 69.46%; % strength 98.51% by quantitative HPLC.
Alternative Reverse Drown-out Work-up A sample of the 'end of chlorination' mixture (100 ml, 0.2586 mol) was heated to 65–70° C. and aliquots of the solution were added to a stirred slurry of potassium bicarbonate (32 g) in potassium bicarbonate solution (20% strength; 48.54 g) at 60° C. over 30 minutes. At the end of the addition, water (40 g) was charged. The mixture was then separated at 60° C., the lower aqueous layer being back-extracted with fluorobenzene (40 ml). The combined fluorobenzene phases were then dried by azeotropic distillation at 85–90° C. Slow addition of cyclohexane (61.4 g) at 80° C. gave a dark red solution which was then slowly cooled to ambient temperature. Further cooling to 0–5° C. gave a beige precipitate which was filtered, washed with n-hexane (26 g), pulled dry on the filter and dried in air to constant weight (25.07 g); $^1$H NMR (CDCl$_3$)δ 3.7 (s,2H); 5.3 (s,2H; 7.2–7.6 (m,4H)ppm; quantitative yield 61.43%; chemical yield 69.15%; % strength 93.78% by quantitative HPLC.
Acid Drown-out Work-up A sample of the 'end of chlorination' mixture (100 ml, 0.2586 mol) was heated to 65–70° C. and potassium iodide (0.18 g) was added in one portion. Potassium bicarbonate solution (20% strength; 48.54 g) was then added slowly followed by portionwise addition of solid potassium bicarbonate (32 g). At the end of the addition, water (40 g) was charged. The mixture was then separated at 60° C., the lower aqueous layer being back-extracted with fluorobenzene (40 ml). The combined fluorobenzene phases were then dried by azeotropic distillation at 85–90° C. Slow addition of cyclohexane (61.4 g) at 80° C. gave a dark red solution which was then slowly cooled to ambient temperature. Further cooling to 0–5° C. gave a beige precipitate which was filtered, washed with n-hexane (26 g), pulled dry on the filter and dried in air to constant weight (24.74 g); $^1$H NMR (CDCl$_3$)δ 3.7(s,2H); 5.3(s,2H); 7.2–7.6(m,4H) ppm; quantitative yield 60.5%; % strength 93.60% by quantitative HPLC.

We claim:

1. A process for the preparation of 3-isochromanone which comprises the steps:
   (a) reacting o-tolylacetic acid with sulphuryl chloride in the presence of a free radical initiator; and
   (b) treating the 2-chloromethylphenylacetic acid so formed with a base.

2. A process for the preparation of 2-chloromethylphenylacetic acid which comprises reacting o-tolylacetic acid with sulphuryl chloride in the presence of a free radical initiator.

3. A process according to claim 2 in which the reaction is carried out in a halogenated aromatic hydrocarbon solvent at a temperature of from 50° C. to 90° C.

4. A process according to claim 2 in which the amount of sulphuryl chloride used is in the range of from 1 to 1.2 moles per mole of o-tolylacetic acid.

5. A process according to claim 2 in which the free radical initiator is 2,2'-azobisisobutyronitrile.

6. A process for the preparation of 3-isochromanone which comprises treating 2-chloromethylphenylacetic acid with a base.

7. A process according to claim 6 in which the base is an alkali metal bicarbonate.

8. A process according to claim 6 which is carried out at a temperature of from 40° C. to 80° C.

9. A process according to claim 6 in which there is present a catalytic amount of an alkali metal iodide.

* * * * *